United States Patent [19]

Inoue et al.

[11] 4,454,357

[45] Jun. 12, 1984

[54] PROCESS FOR PRODUCING O-METHYLATED PHENOLS

[75] Inventors: Yasuhiko Inoue; Tadao Nishizaki, both of Niihama; Satoshi Taguchi, Ibaraki, all of Japan

[73] Assignee: Sumitomo Chemical Company, Limited, Osaka, Japan

[21] Appl. No.: 411,806

[22] Filed: Aug. 26, 1982

[51] Int. Cl.³ ............................................. C07C 37/16
[52] U.S. Cl. ................................... 568/804; 568/794
[58] Field of Search ............... 568/804, 706, 731, 764, 568/774, 794

[56] References Cited

U.S. PATENT DOCUMENTS

| | | | |
|---|---|---|---|
| 2,831,898 | 4/1958 | Ecke et al. | 568/789 |
| 3,290,389 | 12/1966 | Hahn | 568/794 |
| 3,446,856 | 5/1969 | Hamilton | 568/804 |
| 3,479,410 | 11/1969 | Hamilton, Jr. | 568/804 |
| 3,843,606 | 10/1974 | Van Sorge | 568/804 |
| 3,962,126 | 6/1976 | Pecak | 568/804 |
| 3,968,172 | 7/1976 | Ichikawa et al. | 568/804 |
| 4,041,085 | 8/1977 | Farbetti | 568/804 |
| 4,100,207 | 7/1978 | Goodwin et al. | 568/804 |

FOREIGN PATENT DOCUMENTS

| | | | |
|---|---|---|---|
| 907065 | 8/1972 | Canada | 568/804 |
| 43-12337 | of 1968 | Japan . | |
| 56-45427 | 4/1981 | Japan | 568/804 |

OTHER PUBLICATIONS

Klemm et al. "J. Org. Chem" (1980) 45 pp. 4320–4326.

*Primary Examiner*—Werren B. Lone
*Attorney, Agent, or Firm*—Stevens, Davis, Miller & Mosher

[57] ABSTRACT

A process for producing o-methylated phenols useful as raw materials for resins and medicines in high yields comprising reacting methanol with phenols in the presence of a catalyst containing at least one compound selected from the group consisting of (1) magnesium oxide, manganese oxide and iron oxide which are all pre-treated with phenols and (2) magnesium phenolate.

3 Claims, No Drawings

PROCESS FOR PRODUCING O-METHYLATED PHENOLS

This invention relates to a process for producing o-methylated phenols by catalytic reaction of phenols with methanol. More particularly, the invention relates to a process for producing methylated phenols having at least one methyl group, by methylation of at least one ortho-position of phenols with methanol, characterized by using a catalyst comprising at least one compound selected from metal oxides pre-treated with phenols, and a metal phenolate.

Among o-methylated phenols, o-cresol, 2,6-xylenol, and 2,3,6-trimethylphenol are important as raw materials for resins and medicines, in particular. Accordingly, a great number of studies have been made of the production of these o-methylated phenols.

Known processes for alkylating phenols involve those comprising contact reactions of phenols with alcohols in the presence of metal oxides such as aluminum oxide, magnesium oxide, manganese oxide, iron oxide and chromium oxide as catalyst separately or in combination. Taking catalyst performance into consideration, however, these catalysts are unsatisfactory in such respects as activity, selectivity, induction period, catalyst life, etc.

As a result of extensive studies aiming at solving these difficulties in catalysts, the present inventors found that these problems in the alkylating reactions can be corrected to a large extent by using a catalyst containing at least one compound selected from oxides of magnesium, manganese and iron all pre-treated with phenols, and magnesium phenolate. Based on this finding, the present invention has been accomplished.

An object of this invention is to obtain o-methylated phenols in good yields with high selectivities.

Another object of this invention is to produce o-methylated phenols to advantage industrially by using a catalyst, excellent in overall performance characteristics, i.e. improved in activity, selectively, induction period and catalytic life.

In order to achieve these objects, this invention provides a process for producing an o-methylated phenol by reacting methanol with a phenol having at least one hydrogen atom in the ortho-positions on its aromatic ring, characterized by using a catalyst comprising at least one compound selected from the group consisting of (1) magnesium oxide, manganese oxide and iron oxide which are all pre-treated with phenols, and (2) magnesium phenolate.

The starting material phenols for o-methylation used in this invention are phenol compounds, each having at least one hydrogen atom in the ortho-positions on the aromatic ring, represented by the formula,

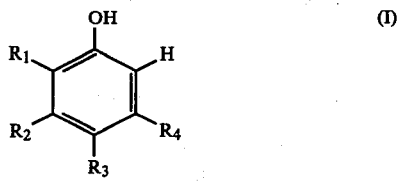

(I)

wherein $R_1$, $R_2$, $R_3$ and $R_4$ represent hydrogen, alkyl of 1 to 5 carbon atoms, hydroxyl, halogen, nitro, methoxy, amino or aromatic hydrocarbon residue such as a substituted or unsubstituted phenyl or naphthyl. Examples of these phenol compounds are phenol, cresols, xylenols, trimethylphenols, phenylphenols, etc.

The alkylating agent used is methanol.

The metal oxides used for the reaction after pretreatment with phenols include those comprising at least one of magnesium oxide, manganese oxide and iron oxide. They may also contain besides the above oxides alone or in combination as main component(s), a compound, for example, silicon oxide, copper oxide, boron oxide, alkali metal, alkaline earth metal, sulfate, chromium oxide or zinc oxide.

Raw materials available for preparations of magnesium oxide, manganese oxide and iron oxide include oxides, hydroxides, halides, nitrates, sulfates, carbonates and organic acid salts, of these metals. Whereas these oxides and hydroxides can be used for preparation of catalyst as such or after simple calcination thereof, these salts are used generally through forming insoluble precipitates by hydrolysis thereof or addition of a base to aqueous solutions thereof, and then via filtration, washing, drying and calcining. Oxides obtained are further granulated each to a desired shape, size and hardness.

The pretreatment of these metal oxides with a phenol is carried out by contacting them with a phenol-containing gas or liquid before or after packing them into a reactor used for the alkylation.

The magnesium phenolate is prepared, for instance, by synthesizing magnesium methylate from metallic magnesium and methanol, followed by refluxing the reaction product with phenol. It is also synthesized by reacting an oxide or hydroxide of magnesium with phenol. The magnesium phenolate is used after being mixed with a metal oxide, incorporated in the surface layers of the oxide granules by impregnation, or coated on the surfaces of the oxide granules. Metal oxides usable for this purpose are common catalyst carriers such as alumina, silica, magnesia, titania, zirconia and the like.

Phenols to be used for the pretreatment of the catalyst are the same in principle as the compounds represented by the formula (I) but include those of which ortho-positioned hydrogen has been replaced by a group of $R_1$ to $R_4$.

These phenols are represented by the formula,

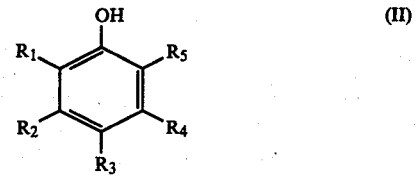

(II)

wherein $R_1$, $R_2$, $R_3$, $R_4$ and $R_5$ represent hydrogen, alkyl or 1 to 5 carbon atoms, hydroxyl, halogen, nitro, methoxy, amino or aromatic hydrocarbon residue such as a substituted or unsubstituted phenyl or naphthyl.

Examples of these phenol compounds are phenol, cresols, xylenols, trimethylphenols, phenylphenols, etc.

These phenols can be used alone or in combination. Moreover, they can be used after being diluted with a non-oxidizing gas, for example, nitrogen, helium or hydrogen. The treatments with these phenols are effected within the range of from around room temperature to 800° C. for approximately 20 minutes to 50 hours, preferably about 30 minutes to 15 hours.

Activation of the catalyst is conducted in a stream of nitrogen, the reaction gas, hydrogen gas, an inert gas or a reducing atmosphere; at temperatures of 100°–600° C., preferably 150°–550° C., for 30 minutes to 100 hours. In particular, by the activating treatment at a temperature of 300° C. or above with steam, the induction period for catalyst activation can be reduced without shortening the catalyst life. Activation temperatures below 300° C., though capable of reducing the induction period, tend to shorten the catalyst life. The activation temperature is not particularly limited provided that it is 300° C. or above; however, for industrial operations, the activation at approximately 300°–700° C. generally gives favorable results.

Steam may be used alone or in combination with the other gas.

In the latter case, while the steam concentration in steam-containing gas is under no particular restriction, low concentrations of the steam tend generally to prolong the period required for activation.

The gas used in combination with steam for the activation may be inert gas, including nitrogen and carbon dioxide.

The catalyst of which activity has been deteriorated by using for the reaction is regenerated by treatment with an oxygen-containing gas or with a mixed gas of oxygen-containing gas and steam to convert into oxides or hydroxides, followed by treatment with the phenol mentioned above.

Although it is difficult to give a clear theoretical interpretation of the effect of the catalyst pre-treated with said phenol or of the catalyst in which said phenolate is incorporated, the presence of some phenolate or compound generated by said pretreatment in advance of the reaction on the catalyst surface seems to provide sites favorable for catalytic activity and selectivity when the alkylating agent and the compound to be alkylated come close to each other during the reaction.

In the process of this invention, the feed ratio by mole of the phenol to methanol is suited to be 4:1 to 1:10, preferably 3:1 to 1:8. For attaining the maximum yield of methylated product, methanol is desired to use in amounts of 2–4 moles per one atom of the hydrogen to be methylated of the phenol. For example, in order to obtain 2,6-xylenol in a high yield by methylation of phenol with methanol, it is desirable to use 4–8 moles of methanol per mole of phenol. The rate of raw material feed to the reactor is desirably 0.2–10 $hr^{-1}$ in liquid space velocity. The liquid space velocity is generally suited to be higher for higher reaction temperature and to be lower for lower reaction temperature. It is also possible to incorporate into the feedstock an inert gas such as nitrogen or a reducing gas such as hydrogen or carbon monoxide. Incorporation of water into the feedstock contributes to further extending the catalyst life and inhibiting undesirble decomposition of methanol.

Reaction temperature in the process of this invention ranges from 300° to 570° C., preferably from 340° to 530° C. The reaction temperature, if below said lower limit, results in unsatisfactory conversion, not filling practical purpose, when the usual reaction mode is applied, and if above said upper limit, tends to deteriorate the selectivity that gives the objective product.

The reaction can be carried out in either liquid phase or gas phase, under any of raised pressure, atmospheric pressure and reduced pressure, employing any form of catalyst bed of fixed, moving or fluidized; however a fixed bed of catalyst is generally employed.

Referring to the following Examples, this invention will be illustrated in more detail: however, it is not limited by the details of these Examples.

Performance characteristics of catalysts in Examples 1–4 and 6–10 are expressed in conversion of phenol and selectivity to 2,6-xylenol, which are defined as follows:

Conversion (mole %) = Conversion of phenol (mole %) =

$$\left(1 - \frac{\text{quantity of phenol unreacted (mole)}}{\text{quantity of phenol charged (mole)}} \times 100\right)$$

Selectivity to 2,6-xylenol based on phenol =

$$\frac{\text{quantity of 2,6-xylenol produced (mole)}}{\text{quantity of phenol charged (mole) } - \text{ quantity of phenol unreacted (mole)}} \times 100$$

Selectivity to 2,6-xylenol based on methanol =

$$\frac{2 \times \text{quantity of 2,6-xylenol produced (mole)}}{\text{quantity of methanol charged (mole) } - \text{ quantity of methanol unreacted (mole)}} \times 100$$

Peformance characteristics of catalysts in Example 5 are expressed in conversion of m-cresol and selectivity to 2,3,6-trimethylphenol, which are defined similarly to the above equations.

The apparatus used for alkylation experiments in the following Examples comprises a feed pump for a phenol, feed pump for methanol, vaporizer for raw material mixtures, quartz glass reactor, and section for condensing product vapor.

EXAMPLE 1

The quartz glass reactor, after 20 ml of a granular catalyst (10–20 mesh) had been packed in the middle section thereof, was set in an electric furnace.

The catalyst, a commercial magnesium oxide, was then treated with phenol alone fed to the reactor at a rate of 10 ml/hr for 3 hours while keeping the catalyst bed temperature at 500° C.

Then, phenol, methanol and water (molar ratio 1:5:1.7) were fed into the reactor at a liquid space velocity of 1.65 $hr^{-1}$ and at the same catalyst bed temperature to produce 2,6-xylenol. The results are shown in Table 1, wherein results of the reaction conducted as Comparative Example 1, in the same manner as in Example 1 except that the catalyst pretreatment with phenol was not carried out are shown.

TABLE 1

|  | Catalyst | Reaction temp. (°C.) | Liquid S.V. ($hr^{-1}$) | Conversion (mole %) | Selectivity to 2,6-xylenol (mole %) | |
|---|---|---|---|---|---|---|
|  |  |  |  |  | Based on $C_6H_5OH$ | Based on $CH_3OH$ |
| Example 1 | Phenol-treated MgO | 500 | 1.65 | 100 | 92 | 78 |
| Comparative | MgO | 500 | 1.65 | 86 | 65 | 35 |

TABLE 1-continued

| Catalyst | Reaction temp. (°C.) | Liquid S.V. (hr$^{-1}$) | Conversion (mole %) | Selectivity to 2,6-xylenol (mole %) Based on C$_6$H$_5$OH | Based on CH$_3$OH |
|---|---|---|---|---|---|
| Example 1 | | | | | |

EXAMPLE 2

Similarly to Example 1, methylation of phenol for producing 2,6-xylenol was conducted but using MnO$_2$ as catalyst and setting the catalyst treatment and reaction temperature at 430° C. and the liquid space velocity at 1.13 hr$^{-1}$. The results are shown in Table 2 together with results of Comparative Example 2 operated as Example 2 but without the catalyst pretreatment with phenol.

TABLE 2

| | Catalyst | Reaction temp. (°C.) | Liquid S.V. (hr$^{-1}$) | Conversion (mole %) | Selectivity to 2,6-xylenol (mole %) Based on C$_6$H$_5$OH | Based on CH$_3$OH |
|---|---|---|---|---|---|---|
| Example 2 | Phenol-treated MnO$_2$ | 430 | 1.13 | 100 | 90 | 75 |
| Comparative Example 2 | MnO$_2$ | 430 | 1.12 | 97 | 75 | 56 |

EXAMPLE 3

Magnesium oxide, immersed in o-cresol at 120° C. for 2 hours, was packed in the reactor mentioned above and was exposed to a stream of nitrogen at the same temperature as of the subsequent reaction (480° C.).

Reaction for producing 2,6-xylenol from phenol and methanol was conducted similarly to Example 1. The results are shown in Table 3 together with results of Comparative Example 3 operated as Example 3 but without the catalyst pretreatment with o-cresol.

TABLE 3

| | Catalyst | Reaction temp. (°C.) | Liquid S.V. (hr$^{-1}$) | Conversion (mole %) | Selectivity to 2,6-xylenol (mole %) Based on C$_6$H$_5$OH | Based on CH$_3$OH |
|---|---|---|---|---|---|---|
| Example 3 | o-Cresol-treated MgO | 480 | 1.65 | 100 | 94 | 82 |
| Comparative Example 3 | MgO | 480 | 1.65 | 57 | 44 | 13 |

EXAMPLE 4

Similarly to Example 1, methylation of phenol for producing 2,6-xylenol was conducted but using Fe$_2$O$_3$ as catalyst treated with phenol alone feeding at a rate of 10 ml/hr and at a temperature of 370° C. for 3 hours, and feeding phenol, methanol, and water (molar ratio 1:3:1.1) at a liquid space velocity of 1.14 hr$^{-1}$ and at a temperature of 370° C. The results are shown in Table 4 together with results of Comparative Example 4 operated as Example 4 but without the catalyst pretreatment with phenol.

TABLE 4

| | Catalyst | Reaction temp. (°C.) | Liquid S.V. (hr$^{-1}$) | Conversion (mole %) | Selectivity to 2,6-xylenol (mole %) Based on C$_6$H$_5$OH | Based on CH$_3$OH |
|---|---|---|---|---|---|---|
| Example 4 | Phenol-treated Fe$_2$O$_3$ | 370 | 1.14 | 91 | 87 | 75 |
| Comparative Example 1 | Fe$_2$O$_3$ | 370 | 1.14 | 82 | 54 | 43 |

EXAMPLE 5

Using magnesium oxide as catalyst treated with m-cresol at 420° C. for 3.5 hours, methylation of m-cresol for producing 2,3,6-trimethylphenol was conducted at 450° C. by feeding m-cresol and methanol (molar ratio 1:7) into the reactor at a liquid space velocity of 0.74 hr$^{-1}$. The results are shown in Table 5 together with results of Comparative Example 5 operated as Example 5 but without the catalyst pretreatment with m-cresol.

TABLE 5

| | Catalyst | Reaction temp. (°C.) | Liquid S.V. (hr⁻¹) | Conversion (mole %) | Selectivity to 2,3,6-trimethylphenol (mole %) | |
|---|---|---|---|---|---|---|
| | | | | | Based on m-cresol | Based on CH₃OH |
| Example 5 | m-Cresol-treated MgO | 450 | 0.74 | 100 | 94 | 87 |
| Comparative Example 5 | MgO | 450 | 0.74 | 94 | 91 | 78 |

EXAMPLE 6

A powder of commercial magnesium oxide (80 g) calcined at 550° C. and 282 g of phenol were charged in a ball mill and mixed at 150° C. for 16 hours. Phenol was thoroughly removed by vacuum evaporation to give magnesium phenolate-containing magnesium oxide of particle sizes 10–16 mesh.

This magnesium oxide was packed as catalyst in the middle section of the reactor, and methylation of phenol for producing 2,6-xylenol was conducted at 500° C. by feeding phenol, methanol and water (molar ratio 1:5:1:1.7) into the reactor at a liquid space velocity of 1.65 hr⁻¹. The results are shown in Table 6 together with the results of Comparative Example 1 shown in Table 1.

TABLE 6

| | Catalyst | Reaction temp. (°C.) | Liquid S.V. (hr⁻¹) | Conversion (mole %) | Selectivity to 2,6-xylenol (mole %) | |
|---|---|---|---|---|---|---|
| | | | | | Based on C₆H₅OH | Based on CH₃OH |
| Example 6 | Mg-phenolate-containing MgO | 500 | 1.65 | 100 | 97 | 85 |
| Comparative Example 1 | MgO | 500 | 1.65 | 86 | 65 | 35 |

EXAMPLE 7

To 300 ml of methanol thoroughly dehydrated was added 0.5 g of iodine. While keeping the solution at 50° C., 36.5 g of metallic magnesium strips were added in limited amounts so as not to cause a vigorous evolution of hydrogen. After evolution of hydrogen had ceased, the solution was refluxed for 3 hours, then cooled, and evaporated in a rotary evaporator at 40° C. for 5 hours to remove methanol and to give magnesium methylate.

A mixture of 48.5 g of this magnesium methylate and 105 g of phenol was suspended in 150 ml of n-heptane. The suspension was heated to reflux n-heptane at 98° C. for 10 hours, then cooled, and evaporated in a rotary evaporator to remove n-heptane and methanol, thereby giving 110 g of magnesium phenolate.

This phenolate (10 g) was thoroughly mixed with 90 g of magnesium oxide powder, and the mixture was granulated by pressure forming, crushed and sized to obtain 10–16 mesh granules of magnesium phenolate-containing magnesium oxide.

Using 20 ml of this magnesium oxide as catalyst, methylation of phenol into 2,6-xylenol was conducted at 490° C. by feeding phenol, methanol and water (molar ratio 1:5:1.7) into the reactor at a liquid space velocity of 1.85 hr⁻¹. The results are shown in Table 7.

TABLE 7

| | Catalyst | Reaction temp. (°C.) | Liquid S.V. (hr⁻¹) | Conversion (mole %) | Selectivity to 2,6-xylenol (mole %) | |
|---|---|---|---|---|---|---|
| | | | | | Based on C₆H₅OH | Based on CH₃OH |
| Example 7 | Mg-phenolate + MgO | 490 | 1.85 | 100 | 93 | 83 |

EXAMPLE 8

Magnesium methylate (48.5 g) and magnesium phenolate (56.0 g) both prepared in the same ways as in Example 7 were thoroughly mixed in a mortar, then granulated by pressure forming, crushed and sized to obtain 10–16 mesh granules.

Using 20 ml of the granules, methylation of phenol into 2,6-xylenol was conducted at 490° C. by feeding phenol, methanol and water (molar ratio 1:5:1.7) into the reactor at a liquid space velocity of 1.65 hr⁻¹. The results are shown in Table 8.

TABLE 8

| | Catalyst | Reaction temp. (°C.) | Liquid S.V. (hr⁻¹) | Conversion (mole %) | Selectivity to 2,6-xylenol (mole %) | |
|---|---|---|---|---|---|---|
| | | | | | Based on C₆H₅OH | Based on CH₃OH |
| Example 8 | Mg-methylate + | 490 | 1.65 | 100 | 96 | 86 |

TABLE 8-continued

| Catalyst | Reaction temp. (°C.) | Liquid S.V. (hr$^{-1}$) | Conversion (mole %) | Selectivity to 2,6-xylenol (mole %) | |
|---|---|---|---|---|---|
| | | | | Based on $C_6H_5OH$ | Based on $CH_3OH$ |
| Mg-phenolate | | | | | |

EXAMPLE 9

A magnesium oxide catalyst (20 ml) treated with phenol in the way of Example 1 was activated in the reactor at 500° C. for 20 hours by passing steam (200 ml/min) and nitrogen gas (60 ml/min).

Whereas the catalyst of Example 1 required 37 hours, from the start of methylating reaction of phenol, for attaining a conversion of 100% and a selectivity to 2,6-xylenol of 92.7% based on phenol, the catalyst of this Example, which received the above activation treatment, required only 26 hours for attaining the corresponding conversion and selectivity.

EXAMPLE 10

A mixture of 282 g of phenol and 86 g of magnesium methylate prepared from metallic magnesium and methanol was heated at 70° C. to make a solution, to which 300 ml of n-heptane was added. The mixture was refluxed at 98° C. for 24 hours, then cooled, and evaporated in a rotary evaporator to remove heptane, phenol and methanol, thereby giving 170 g of magnesium phenolate.

This phenolate (10 g) was thoroughly mixed with 90 g of magnesium oxide powder, and the mixture was granulated by pressure forming, crushed and sized to obtain 10-16 mesh granules.

The granules (20 ml) were packed as catalyst in the reactor and activated at 400° C. for 3 hours by passing nitrogen gas (30 ml/min) and steam (33.0 ml/hr as water).

Then, methylation of phenol was conducted at 500° C. by feeding methanol, phenol and water (molar ratio 5:1:1.69) into the reactor at a liquid space velocity of 1.65 hr$^{-1}$. As a result, the induction period was 30 hours. When the reaction temperature was kept at 490° C., the conversion of phenol was 94% and the selectivity to 2,6-xylenol was 91% based on phenol and 79% based on methanol.

COMPARATIVE EXAMPLE 6

Methylation of phenol was conducted in the same manner as in Example 10 without activating the catalyst. The results indicated an induction period of 40 hours.

EXAMPLE 11

Commercial granular manganese dioxide, calcined at 500° C. for 5 hours, was crushed and sized to obtain 10-16 mesh granules.

The granules (20 ml) were packed in the reactor and pretreated at 450° C. for 3 hours by passing nitrogen gas (60 ml/min) and phenol vapor (10 g/hr) and subsequently at 430° C. for 8 hours by passing nitrogen gas (30 ml/min) and steam (20 ml/hr as water).

Methylation of phenol was then conducted in the reactor at 430° C. by feeding methanol, phenol and water (molar ratio 5:1:1.41) at a liquid space velocity of 1.20 hr$^{-1}$. As a result, the induction period was 15 hours.

COMPARATIVE EXAMPLE 7

Methylation of phenol was conducted in the same manner as in Example 11 without activating the catalyst. The results indicated an induction period of 25 hours.

What is claimed is:

1. A process for producing an o-methylated phenol comprising reacting methanol with a phenol represented by the formula,

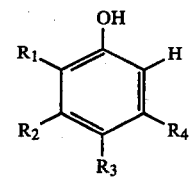

wherein $R_1$, $R_2$, $R_3$ and $R_4$ represent hydrogen, alkyl of 1 to 5 carbon atoms, hydroxyl, halogen, nitro, methoxy, amino or aromatic hydrocarbon residue, characterized by using a catalyst containing at least one compound selected from the group consisting of (1) magnesium oxide, manganese oxide and iron oxide which are all pre-treated with a phenol represented by the formula,

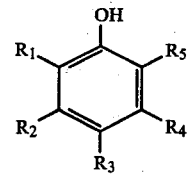

wherein $R_1$, $R_2$, $R_3$, $R_4$ and $R_5$ represent hydrogen, alkyl of 1 to 5 carbon atoms, hydroxyl, halogen, nitro, methoxy, amino or aromatic hydrocarbon residue, and (2) magnesium phenolate, wherein the temperature of the reaction is from 300° to 570° C. and wherein the feed ratio by mole of phenol to methanol is 4:1 to 1:10.

2. The process for producing an o-methylated phenol according to claim 1, wherein the pre-treatment with a phenol is carried out with a temperature range of room temperature to 700° C.

3. The process for producing an o-methylated phenol according to claim 1, wherein the catalyst is further treated for activation with steam at a temperature of 300° C. or above.

* * * * *

UNITED STATES PATENT AND TRADEMARK OFFICE
CERTIFICATE OF CORRECTION

PATENT NO. :  4,454,357
DATED      :  June 12, 1984
INVENTOR(S) : Yasuhiko INOUE et al It is certified that error appears in the above-identified patent and that said Letters Patent is hereby corrected as shown below:

On the title page;

In the heading of the patent, the priority data should read as follows:

--

[30]   Foreign Application Priority Data

Aug. 31, 1981 [JP]   Japan ........... 56-137557
    Jan. 28, 1982 [JP]   Japan ........... 57-13151
    May 31, 1982 [JP]   Japan ........... 57-93792

--

Signed and Sealed this

Twenty-fifth Day of June 1985

[SEAL]

Attest:

DONALD J. QUIGG

Attesting Officer      Acting Commissioner of Patents and Trademarks